(12) United States Patent
Niemeyer et al.

(10) Patent No.: US 11,338,288 B2
(45) Date of Patent: May 24, 2022

(54) PERISTALTIC PUMP AND ANALYZER FOR TESTING A SAMPLE

(71) Applicant: BOEHRINGER INGELHEIM VETMEDICA GMBH, Ingelheim am Rhein (DE)

(72) Inventors: Axel Niemeyer, Bielefeld (DE); Hannah Schmolke, Didderse (DE); Guenter Bruckmann, Wuerselen (DE); Harald Pauls, Eschweiler (DE); Ursula Amberg, Moenchengladbach (DE); Guenter Scholz, Pulheim-Dansweiler (DE); Rene Wirt, Solingen (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 166 days.

(21) Appl. No.: 16/585,864

(22) Filed: Sep. 27, 2019

(65) Prior Publication Data

US 2020/0101457 A1 Apr. 2, 2020

(30) Foreign Application Priority Data

Oct. 1, 2018 (EP) ..................................... 18197834

(51) Int. Cl.
*B01L 3/00* (2006.01)
*F04B 43/12* (2006.01)

(52) U.S. Cl.
CPC ...... *B01L 3/50273* (2013.01); *F04B 43/1223* (2013.01); *B01L 2200/025* (2013.01); *B01L 2300/0816* (2013.01); *B01L 2300/123* (2013.01)

(58) Field of Classification Search
CPC ............................. B01L 3/50273; F04B 43/12
See application file for complete search history.

(56) References Cited

U.S. PATENT DOCUMENTS

| | | | |
|---|---|---|---|
| 5,096,669 A | 3/1992 | Lauks et al. | |
| 5,863,502 A | 1/1999 | Southgate et al. | |
| 6,645,176 B1 | 11/2003 | Christenson et al. | |
| 7,123,029 B2 | 10/2006 | Frey et al. | |
| 7,914,655 B2 | 3/2011 | Frey et al. | |
| 8,079,836 B2 | 12/2011 | Gao et al. | |
| 9,110,044 B2 | 8/2015 | Gumbrecht et al. | |

(Continued)

FOREIGN PATENT DOCUMENTS

| | | |
|---|---|---|
| AU | 2003204460 B2 | 6/2003 |
| CN | 1984716 A | 6/2007 |
| CN | 102409039 A | 4/2012 |

OTHER PUBLICATIONS

Yi Hui et al.: "Automated liquid operation method for microfluidic heterogeneous immunoassay", Talanta, Elsevier B.V., Dec. 1, 2012, pp. 52-56, vol. 105, Amsterdam, Netherlands.

(Continued)

*Primary Examiner* — Matthew D Krcha
(74) *Attorney, Agent, or Firm* — David S. Safran; Roberts Calderon Safran & Cole, P.C.

(57) ABSTRACT

A peristaltic pump and an analyzer for testing a biological sample, wherein the pump includes a pump head that is constructed as a screwless assembly, wherein the pump includes a bayonet and/or a beam coupling, and/or wherein rollers of the pump are configured to be pivoted about corresponding pivot axes that intersect with the roller axes.

14 Claims, 10 Drawing Sheets

(56) References Cited

U.S. PATENT DOCUMENTS

| | | |
|---|---|---|
| 2003/0026719 A1 | 2/2003 | Hahn et al. |
| 2003/0143754 A1 | 7/2003 | Lum et al. |
| 2006/0093836 A1 | 5/2006 | Huang et al. |
| 2008/0031778 A1 | 2/2008 | Kramer |
| 2008/0050287 A1 | 2/2008 | Araragi et al. |
| 2008/0241890 A1 | 10/2008 | Gumbrecht et al. |
| 2008/0304982 A1* | 12/2008 | Miyazaki ............... F04B 43/12 417/412 |
| 2009/0165876 A1 | 7/2009 | Atkin et al. |
| 2010/0304986 A1 | 12/2010 | Chen et al. |
| 2012/0009667 A1 | 1/2012 | Peterson et al. |
| 2013/0087226 A1 | 4/2013 | Weber |
| 2013/0240140 A1 | 9/2013 | Kurowski et al. |
| 2013/0251561 A1 | 9/2013 | Ramirez, Jr. et al. |
| 2013/0287613 A1 | 10/2013 | Gould et al. |
| 2014/0105766 A1 | 4/2014 | Sharman |
| 2014/0356205 A1* | 12/2014 | Baxter ................... F04B 43/12 417/477.7 |
| 2015/0080798 A1* | 3/2015 | Nzike ................. F04B 43/1284 604/151 |
| 2015/0306596 A1 | 10/2015 | Thompson et al. |
| 2017/0058881 A1 | 3/2017 | Sugiura et al. |

OTHER PUBLICATIONS

Gourlay et al.: "Development of a portable blood salvage and autotransfusion technology to enhance survivability of personnel requiring major medical interventions in austere or military environments", Journal of Royal Army Medical Corps, Oct. 26, 2017, pp. 96-102, United Kingdom.

Anonymous: "Servo Couplings for High-Tech Systems—Tech Briefs", https://www.techbriefs.com/component/content/article/tb/features/articles/26432, Feb. 1, 2017, pp. 1-5.

Anonymous, "Polypropylene-Is it different from Polyethylene?", https://www.globalplasticsheeting.com/our-blog-resource-library/bid/92169/polypropylene-is-it-different-from-polythylene, posted by Nana Hinsley on Nov. 10, 2014, 5 pages.

* cited by examiner

PERISTALTIC PUMP AND ANALYZER FOR TESTING A SAMPLE

BACKGROUND OF THE INVENTION

Field of the Invention

The present invention relates to a peristaltic pump for conveying a fluid within a cartridge and to an analyzer for testing a biological sample.

The present invention deals with analyzing and testing a sample, in particular from a human or animal, preferably for analytics and diagnostics, e.g. with regard to the presence of diseases and/or pathogens and/or for determining blood counts, antibodies, hormones, steroids or the like.

The present invention is particularly useful within the field of bioanalytics. However, a food sample, an environmental sample or another sample may also be tested in accordance with the features of the present invention discussed herein, in particular for environmental analytics or food safety and/or for detecting other substances.

Preferably, by means of the present invention, at least one analyte (target analyte) of a sample can be determined, identified or detected. In particular, the sample can be tested for qualitatively or quantitatively determining at least one analyte, e.g. in order to detect or identify a disease and/or pathogen.

Within the meaning of the present invention, analytes are in particular nucleic-acid sequences, in particular DNA sequences and/or RNA sequences, and/or proteins, in particular antigens and/or antibodies. Preferably, by means of the present invention, nucleic-acid sequences and/or proteins can be determined, identified or detected as analytes of a sample. Mostly preferred, the present invention deals with systems, devices and other apparatuses for carrying out a nucleic-acid assay for detecting a nucleic-acid sequence and/or a protein essay for detecting or identifying a protein.

The present invention preferably deals with what are known as point-of-care systems, e.g. within particular mobile systems, devices or other apparatuses, and deals with methods for carrying out tests on a sample at the sampling side and/or independently or away from a central laboratory or the like. Preferably, point-of-care systems can be operated autonomously or independently of a mains network for supplying electrical power.

Description of the Related Art

U.S. Pat. No. 5,096,669 discloses such point-of-care systems for testing a biological sample. The system comprises a single-use cartridge and an analyzer. Once the sample has been received, the cartridge is inserted into the analyzer in order to carry out the test. The cartridge comprises a microfluidic system and a sensor apparatus comprising electrodes to test the sample.

Furthermore, International Patent Application Publication WO 2006/125765 A1 discloses a point-of-care system for integrated or automated DNA or protein analysis, comprising a single-use cartridge and an analyzer for fully automatically processing and evaluating molecular-diagnostic analysis using the cartridge.

Usually, pumps, in particular peristaltic pumps, are used to convey the sample or other fluids in such point-of-care systems.

For example, European Patent EP 1 829 568 B1 and corresponding U.S. Pat. No. 8,079,836 B2 disclose a method for operating a peristaltic pump having a roller head which supports a plurality of rollers, the roller head being brought into contact with a flexible fluid channel of a cartridge and being rotated such that the plurality of rollers contact the fluid channel and cause fluids to flow through the fluid channel.

U.S. Patent Application Publication 2014/0356205 A1 discloses a peristaltic pump comprising a central section with a hub, a plurality of arms coupled to the central section and a plurality of rollers, one roller coupled to each of the plurality of arms. The rolling surface of the rollers is arranged to engage a polymer sheet or a flexible tubing.

U.S. Patent Application Publication 2017/0058881 A1 discloses a micro peristaltic pump comprising a rotor with rollers that are pressed against a circular arc shaped flow path in a microfluidic chip, wherein the rotor is rotary-driven by a driving motor and the circular arc shaped flow path is caused to make a peristaltic motion by rotation of the rotor to send a liquid in the flow path.

SUMMARY OF THE INVENTION

The problem addressed by the present invention is to provide an improved peristaltic pump and an improved analyzer comprising such a pump, preferably wherein an improved, in particular reliable, simple, gentle, hygienic and/or energy-efficient, conveyance of fluid and/or a robust and easy construction of the pump is made possible or facilitated.

The above problem is solved by a peristaltic pump and an analyzer as described herein. Advantageous developments of the present invention are subject of the dependent claims.

For the conveyance of a fluid within a cartridge for testing an in particular biological sample, it is proposed that a peristaltic pump comprising a preferably electric motor and a pump head is used, preferably wherein the pump is in contact or can be brought into contact with a pump apparatus of the cartridge for conveying a sample and/or another fluid within the cartridge.

According to one aspect of the present invention, the pump head of the pump is constructed as a screwless assembly, preferably wherein all parts of the pump head are connected to each other by means of a snap/clip-on connection. This provides a simple, robust and/or cost-effective construction and/or facilitates a fast, cost-effective and easy assembly of the pump head.

The terms "snap", "clip" and/or "snap/clip-on connection" is preferably understood to refer to an assembly/connection method wherein at least two parts are assembled/connected to one another—in particular in a force-fitting and/or form-fitting manner—using the elasticity/flexibility of the parts to be assembled/connected and/or without using (additional) fastening elements, such as nails, screws, bolts or the like.

In particular, at least two parts are snap-fitted/clipped together by pushing the interlocking components of these parts together and/or into one another, preferably wherein at least one interlocking component is (temporarily) deformed.

The pump, in particular the pump head, preferably comprises a plurality of preferably cone-shaped rollers for contacting the cartridge, in particular for acting on the pump apparatus of the cartridge, preferably wherein the rollers are clipped in the pump head. Mostly preferred, the rollers are clipped in brackets, which in turn are clipped in a main body of the pump head.

According to another aspect of the present invention, which can also be implemented independently, the pump head comprises a plurality of pivotable brackets for the rollers, wherein each of the rollers is mounted to one of the brackets and can be rotated about a roller axis and wherein each of the brackets is mounted to the main body of the pump head and can pivot about a pivot axis relative to the main body.

Due to the pivotable brackets, it is possible to pivot the rollers, preferably independently from one another and/or about pivot axes that are tranverval, in particular perpendicular, to the corresponding roller axes.

In this way, it is possible to adapt the pump head, i.e. its frontside (the side facing the cartridge), to the surface of the cartridge, in particular such that unevennesses or asperities can be compensated for and/or smoothed out.

According to a further aspect of the present invention, which can also be realized independently, the pivot axes of the brackets run through the associated/corresponding rollers. Mostly preferred, the roller axes and the pivot axes intersect with each other. In this way, the force transmission from the pump to the cartridge is improved. In particular, no torque is caused and an unwanted tilting/lifting of the rollers relative to the surface of the cartridge is prevented.

Mostly preferred, the pivot axes run through the broader half of the cone-shaped rollers and/or at a level between ¼ and ⅓ of the height of the rollers, measured from its broader bottom. This allows a constant pressure (distribution) along the roller axes as the cartridge might bend (locally) when brought into contact with the pump head.

According to another aspect of the present invention, which can also be realized independently, the pump comprises a coupling apparatus for (mechanically) connecting the pump head to the motor, wherein the coupling apparatus is constructed as a bayonet coupling. This allows an easy and fast assembly/disassembly of the pump.

Preferably, the coupling apparatus comprises a first coupling part and a second coupling part, wherein the coupling parts are connected to one another via a bayonet joint and/or in a detachable manner, in particular such that the assembly/disassembly of the coupling apparatus is screwless and/or can be done without using tools.

Mostly preferred, the coupling apparatus comprises a coupling/inner spring, wherein the coupling parts are pressed apart from one another by means of the coupling/inner spring, in particular such that the bayonet joint cannot accidentally open. In this way, it is prevented that the coupling apparatus falls apart during use of the pump. In particular, it is prevented for the pump head or its second coupling part to decouple from the motor or the first coupling part.

Preferably, the pump, in particular its pump head or coupling apparatus, is compressible and/or the coupling parts can be moved axially to one another, preferably by compressing the coupling/inner spring and/or in order to adjust the force acting on the cartridge and/or such that damaging of the cartridge is prevented.

According to another aspect of the present invention, which can also be realized independently, the coupling apparatus is constructed as a tumbling/flexible/beam coupling, preferably wherein the coupling is flexible/bendable and/or adapted to compensate (angular) misalignment and/or an offset between the pump head and the motor and/or to allow a tumbling motion of the pump head (relative to the motor).

Preferably in addition to its coupling/inner spring, the coupling apparatus might be equipped with an optional tumbling/outer spring, in particular wherein the tumbling/outer spring is embodied as an integrated spring and/or formed by the wall of the coupling apparatus.

The construction of this kind makes it possible to compensate an angular misalignment between the pump and the cartridge, e.g. when the motor axis of the pump is not perpendicular to the cartridge or its main plane.

With other words, due to the flexibility of the pump, in particular its coupling apparatus, and/or due to the pivotable rollers, the (entire) pump head and/or the rollers can be adjusted to the cartridge, in particular to the surface of the cartridge and/or to the orientation of the cartridge relative to the pump.

The proposed analyzer preferably comprises on the one hand a receptacle for the cartridge containing a sample and on the other hand a peristaltic pump for conveyance of the sample or other fluids within the cartridge. In particular, the cartridge can be inserted into the analyzer for testing the sample and/or can be moved, displaced or pressed towards or against the peristaltic pump, in particular its pump head, or vice versa.

In the context of the present invention, the term "analyzer" is preferably understood to refer to a preferably mobile instrument/apparatus, which is designed to chemically, biologically and/or physically tests and/or analyze a sample or a component thereof, preferably in and/or by means of a cartridge containing the sample. The analyzer preferably controls the testing of the sample in and/or by means of the cartridge. In order to carry out the test, the cartridge can be connected to, in particular received by, the analyzer, as already mentioned.

The term "cartridge" is preferably understood to refer to an in particular disposable apparatus or unit which is designed to receive, to store and/or to physically, chemically and/or biologically treat and/or prepare and/or to measure a sample, preferably in order to detect, identify or determine at least one analyte, in particular a protein and/or nucleic-acid sequence, of the sample.

A cartridge within the meaning of the present invention preferably comprises a fluid system having a plurality of channels, cavities and/or valves for controlling the flow through the channels and/or cavities. In particular, a cartridge is designed to be at least substantially planar and/or card-like. Mostly preferred, a cartridge is designed as a (micro)fluidic card and/or as a support/container that can be closed and/or inserted and/or plugged in an analyzer when it contains a sample.

The term "coupling" is preferably understood to refer to an in particular detachable connection between two parts/components, in particular coupling parts, for power/torque transmission.

The term "beam coupling" is preferably understood to refer to a flexible/elastic/bendable coupling and/or a coupling that is adapted to compensate angular and/or parallel misalignment between two parts/components, in particular coupling parts. A beam coupling preferably is at least partially flexible/elastic/bendable and/or comprises a flexible/elastic/bendable part/section/portion, such as a spring, and/or a part/section/portion with reduced stiffness and/or increased elasticity (compared to the other and/or adjacent part/section/portion of the coupling).

The above-mentioned aspects and features of the present invention and the aspects and features of the present invention that will become apparent from the claims and the following description can in principle be implemented independently from one another, but also in any combination.

Other aspects, advantages, features and properties of the present invention will become apparent from the claims and the following description of a preferred embodiment with reference to the accompanying drawings.

DETAILED DESCRIPTION OF THE INVENTION

In the following description, the same reference signs are used for the same and similar parts and components, resulting in corresponding or comparable properties, features and advantages, even if these are not repeatedly described.

Figure 1:
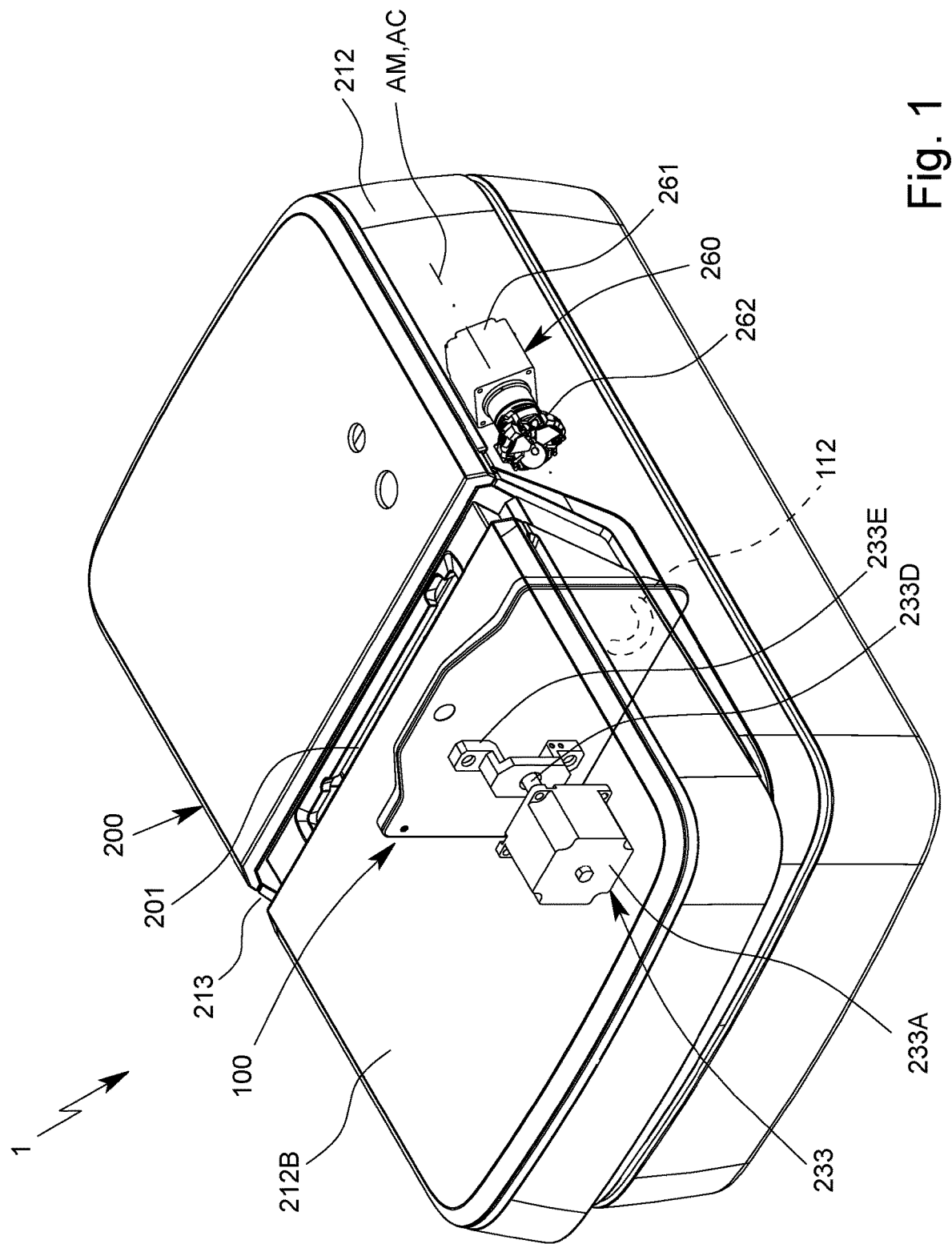
FIG. 1 is a perspective view of a proposed system comprising a proposed analyzer, a cartridge inserted therein and a proposed peristaltic pump.

FIG. 1 is a schematic view of a proposed analysis system 1, a proposed analyzer or analyzer 200 and a proposed pump 260. The analyzer 200 is shown in a transparent manner.

Preferably, the analysis system 1 comprises the analyzer 200 and an apparatus or cartridge 100 for testing an in particular biological sample. In FIG. 1, the cartridge 100 is already inserted into/received by the analyzer 200, in particular such that the test can be conducted.

Figure 3:
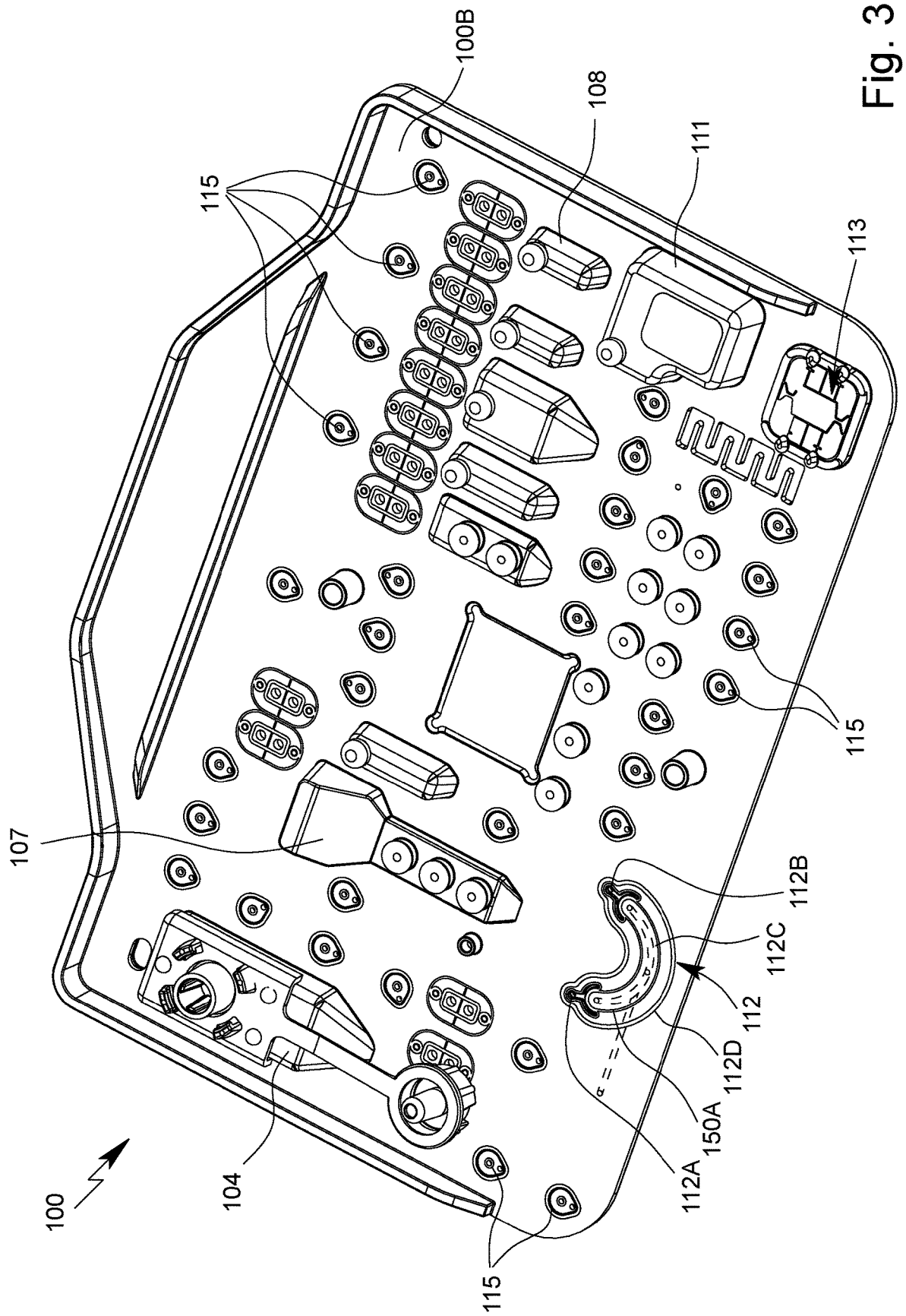
FIG. 3 is a schematic perspective rear view of the cartridge.
Figure 4:
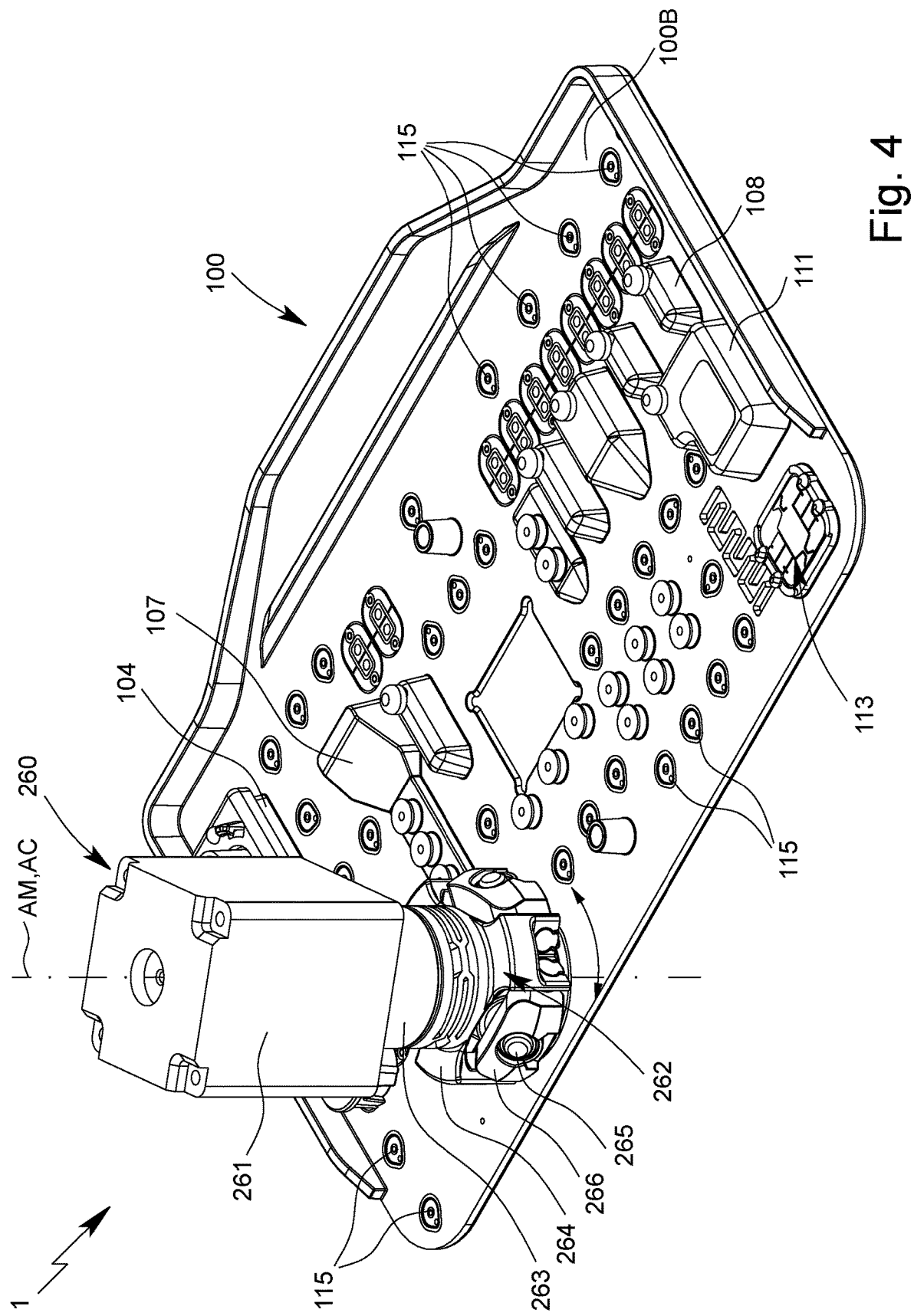
FIG. 4 is a schematic perspective rear view of the cartridge and the proposed peristaltic pump connected thereto.

FIG. 3 is a perspective front view of the cartridge 100, showing its front 100A and FIG. 4 is a perspective rear view thereof, showing its back 100B.

Preferably, the analyzer 200 controls the testing of the sample in particular in and/or on the cartridge 100 and/or is used to evaluate the testing and/or to collect, to process and/or to store measured values from the test.

By means of the analyzer 200 and/or the cartridge 100, an analyte or a plurality of analytes of the sample can be determined, identified or detected, preferably not only qualitatively, but also quantitatively.

Therefore, the sample can in particular be tested for qualitatively and/or quantitatively determining at least one analyte, e.g. in order to detect or identify a disease and/or a pathogen or to determine other values, which are important for diagnostics, for example.

The term "sample" is preferably understood to refer to a sample material that is to be tested and which is in particular taken from a human or animal. Preferably, within the meaning of the present invention, a sample is a fluid, such as saliva, blood, urine or another liquid, preferably from a human or animal, or a component thereof.

Within the meaning of the present invention, a sample may be pretreated or prepared if necessary, or may come directly from a human or animal or the like. A food sample, environmental sample or another sample may optionally also be tested, in particular for environmental analytics, food safety and/or for detecting other substances, preferably natural substances, but also biological or chemical warfare agents, poisons or the like.

A sample within the meaning of the present invention preferably contains one or more analytes, it preferably being possible for the analytes to be identified or detected, in particular qualitatively and/or quantitatively determined. Preferably, within the meaning of the present invention, a sample has target nucleic-acid sequences as analytes, in particular target DNA sequences and/or target RNA sequences, and/or target proteins as analytes, in particular target antigens and/or target antibodies. Preferably, at least one disease and/or pathogen can be detected and/or identified in the sample by qualitatively and/or quantitatively determining the analytes.

The cartridge 100 preferably is at least substantially planar, flat, plate-shaped and/or card-like.

The cartridge 100 preferably comprises an in particular at least substantially planar, flat, plate-shaped and/or card-like main body/support 101, the main body 101 in particular being made of and/or injection-molded from plastic material, in particular polypropylene.

The cartridge 100 preferably comprises two flat sides 100A, 100B. In particular, the front 100A of the cartridge 100 and the back 100B of the cartridge 100 are each a flat side of the in particular planar and/or card-like cartridge 100.

The cartridge 100 preferably comprises at least one film/cover 102 for covering the main body 101 and/or cavities and/or channels formed therein, at least partially, preferably on the front 100A and/or for forming valves or the like.

The cartridge 100 and/or its main body 101, in particular together with its cover 102, preferably forms and/or comprises a fluidic system 103, in the following referred to as the fluid system 103.

The cartridge 100, the main body 101 and/or the fluid system 103 are/is preferably at least substantially vertically oriented in the operating position/state and/or during the test and/or when being inserted in the analyzer 200, as shown in FIG. 1.

The cartridge 100, in particular its fluid system 103, preferably comprises a plurality of cavities, in particular at least one receiving cavity 104, at least one metering cavity 105, at least one intermediate cavity 106, at least one mixing cavity 107, at least one storage cavity 108, at least one reaction cavity 109, at least one (intermediate) temperature-control cavity 110 and/or at least one collection cavity 111, preferably wherein a plurality of these cavities are fluidically interconnected in particular by a plurality of channels.

The cartridge 100, in particular the fluid system 103, preferably comprises at least one pump apparatus 112 and/or at least one sensor apparatus 113.

The sensor apparatus 113 is used in particular for detecting, preferably qualitatively and/or quantitatively determining, the analyte or analytes of the sample, mostly preferred the target nucleic-acid sequences and/or target proteins. Alternatively or additionally, other values may also be collected and/or determined in particular by means of the sensor apparatus 113.

Figure 2:
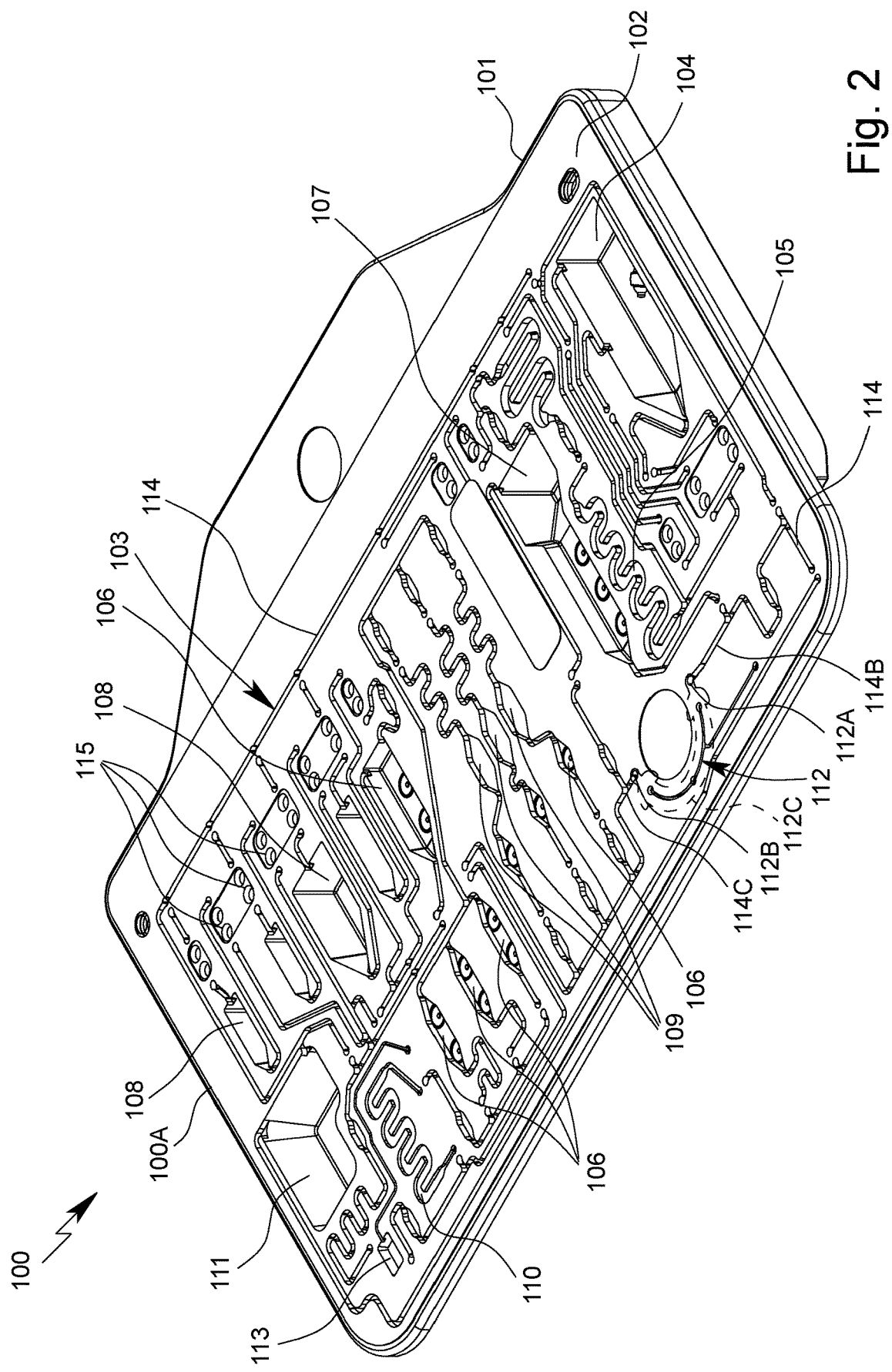
FIG. 2 is a schematic perspective front view of the cartridge.

The cartridge 100, in particular the fluid system 103, preferably comprises a plurality of channels 114 and/or valves 115, as best seen in FIG. 2.

In particular by means of the channels 114 and/or valves 115, the cavities 104 to 111, the pump apparatus 112 and/or the sensor apparatus 113 can be temporarily and/or permanently fluidically interconnected and/or fluidically separated from one another, as required and/or optionally or selectively, in particular such that they are controlled by the analyzer 200.

The cavities 104 to 111 are preferably each fluidic ally linked or interconnected by the plurality of channels 114. In particular, each cavity is linked or connected by at least two associated channels 114, so that the fluid can fill, flow through and/or drain from a respective cavity as required.

The fluid transport or the fluid system 103 is preferably not or not exclusively based on capillary forces, but is preferably essentially based on the effects of gravity and/or pumping forces, compressive forces and/or suction forces that arise and that are preferably generated by the pump apparatus 112.

Mostly preferred, the flow or transport of fluids and the metering are controlled by accordingly opening and closing the valves 115 and/or by accordingly operating the pump apparatus 112, preferably by means of the analyzer 200, in particular its pump 260.

The cartridge 100 is preferably designed as a microfluidic cartridge and/or the fluid system 103 is preferably designed as a microfluidic system.

In the present invention, the term "microfluidic" is preferably understood to mean that the respective volumes of the individual cavities, some of the cavities or all of the cavities 104 to 111 and/or channels 114 are, separately or cumulatively, less than 5 ml or 2 ml, preferably less than 1 ml or 800 µl, in particular less than 600 µl or 300 mostly preferred less than 200 µl or 100 µl.

Preferably, a sample having a maximum volume of 5 ml, 2 ml or 1 ml can be introduced into the cartridge 100 and/or the fluid system 103, in particular the receiving cavity 104.

As already mentioned, the sample or a component thereof and/or a fluid is conveyed within the cartridge 100, in particular fluid system 103, by means of the pump apparatus 112 and/or by accordingly controlling the valves 115.

The pump apparatus 112 is preferably arranged on and/or accessible from the back 100B of the cartridge 100, as shown in FIG. 3.

Preferably, the pump apparatus 112 comprises at least one pump chamber/channel 112C and/or is formed by at least one pump chamber/channel 112C.

The pump apparatus 112, in particular its pump chamber 112C, is preferably designed as a raised portion and/or depression on or in the cartridge 100, in particular its main body 101.

Preferably, the pump apparatus 112, in particular its pump chamber 112C, comprises a wall 112D that is at least partially flexible and/or elastically deformable and/or that is formed by a film or cover.

Mostly preferred, the pump apparatus 112, in particular its pump chamber 112C, is elastically deformable, in particular compressible, at least in part and/or in portions, in particular by means of the pump 260. Preferably, the wall 112D can be pressed onto the main body 101 or the surface thereof, preferably wherein the wall 112D or pump chamber 112C enlarges or resets again automatically and/or by a counter force and/or by a restoring, deflecting or manipulating means.

For this reason, the cartridge 100 and/or pump apparatus 112 might be equipped with a restoring, deflecting or manipulating apparatus 150 for positioning, deflecting or restoring the pump chamber 112C and/or wall 112D.

Figure 9:
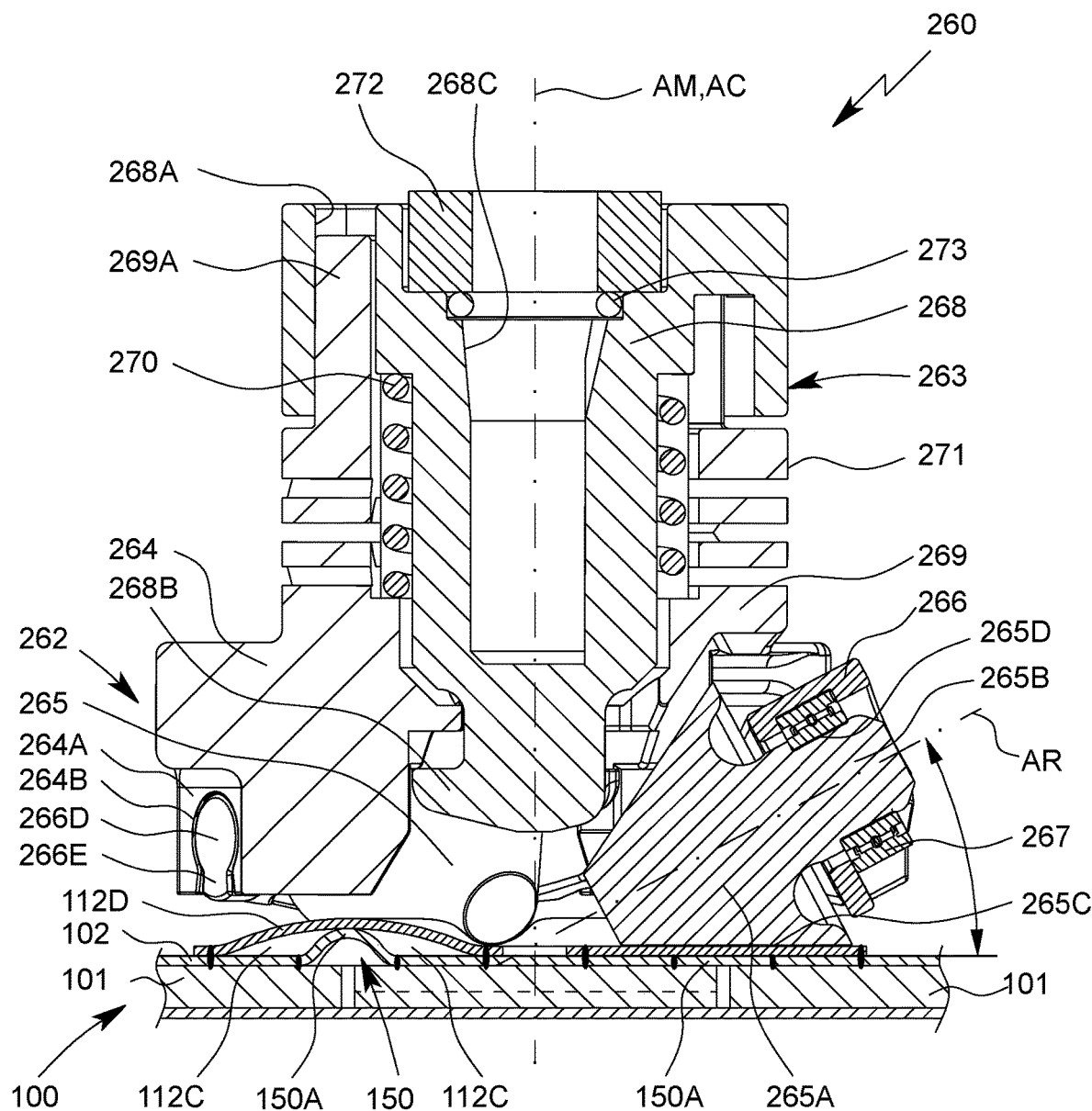
FIG. 9 is a schematic section through the pump when being connected to the partially shown cartridge.
Figure 10:
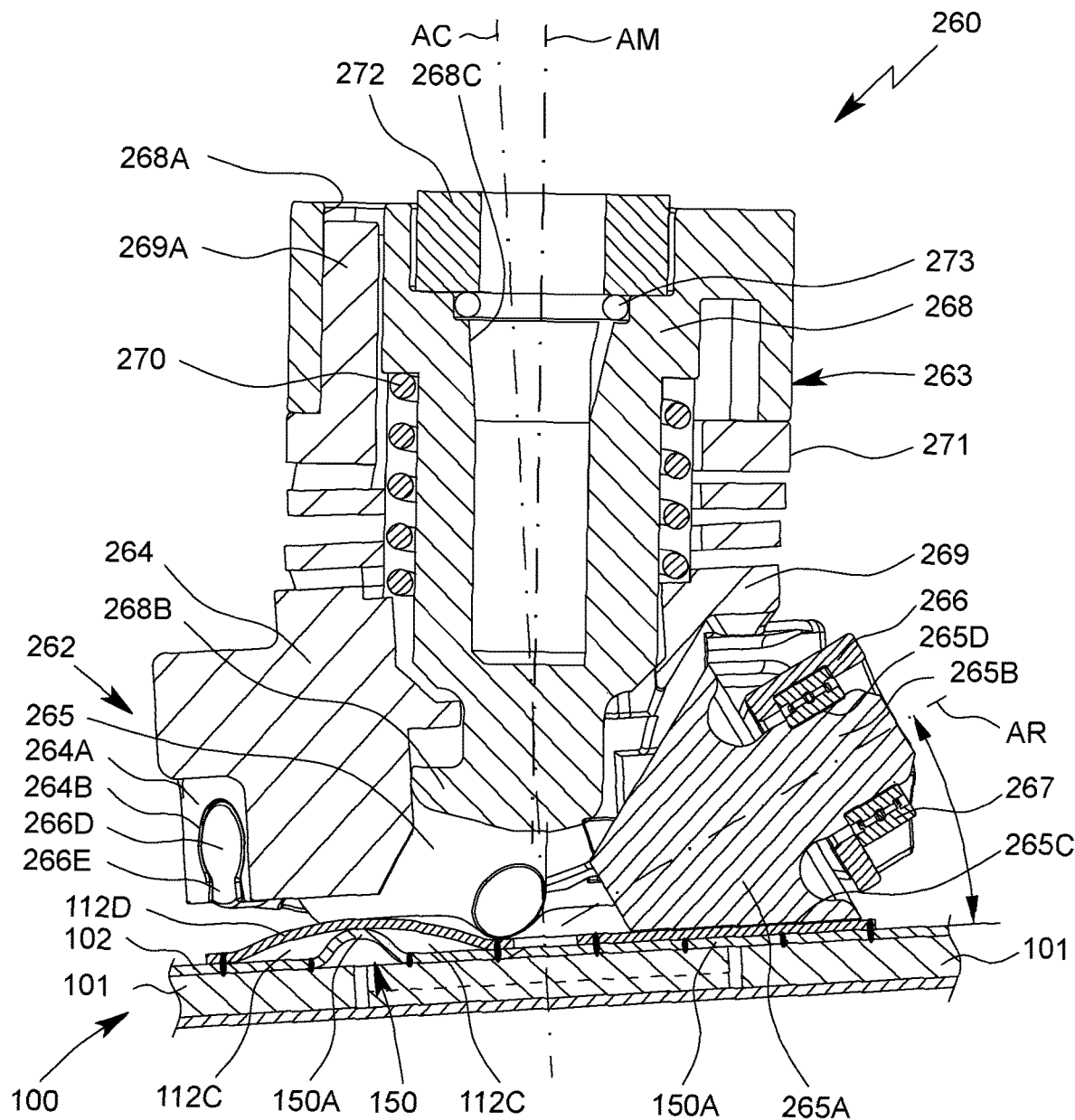
FIG. 10 is a schematic section of the pump according to FIG. 9, when being deflected.

Preferably, the manipulating apparatus 150 comprises a manipulating or deflecting element 150A, preferably wherein the pump chamber 112C is enlarged by means of the manipulating element 150A and/or the wall 112D is raised by means of the manipulating element 150A as shown in FIGS. 9 and 10 that will be described later on.

In particular, the manipulating apparatus 150 is designed to enlarge the pump chamber 112C and/or to raise the wall 112D and/or push the wall 112D away from the main body 101 (again) following its deformation.

Preferably, the wall 112D is formed by a film/sheet arranged on a film/sheet thereunder, such that the pump chamber 112C can be formed therebetween by appropriate welding, as best seen FIGS. 9 and 10.

The manipulating element 150A is in particular raised automatically in order to enlarge the pump chamber 112C and/or to raise the wall 112D. However, other constructional solutions are possible as well.

The pump chamber 112C and/or wall 112D are/is preferably bulged and/or raised relative to the main body 101 or the surface thereof and/or are/is formed as a bead. However, other solutions are possible as well.

Preferably, the pump chamber 112C is curved, in particular arcuate or circular, and/or in the shape of an arc or a circle, as best seen in FIG. 3.

The angle enclosed between the two ends of the pump chamber 112C and/or the angle at the center of the arc formed by the pump chamber 112C is preferably greater than 90°, preferably greater than 120° or 150°, in particular at least substantially 180°, and/or less than 360°, preferably less than 280°, in particular less than 270°.

The pump chamber 112C preferably has and/or defines a volume, in particular a pump volume, for a fluid, in particular the sample and/or reagents, preferably wherein the volume is adaptable, in particular reducible, at least temporarily.

The volume of the pump chamber 112C is preferably greater than 0.5 µl or 1 µl, mostly preferred greater than 3 µl, and/or less 100 µl, mostly preferred less than 50 µl or 20 µl.

As already mentioned, a fluid, in particular the sample, a reagent and/or a gas, can be conveyed through the pump chamber 112C, in particular by temporarily changing the pump volume of the pump chamber 112C and/or by deforming, in particular compressing, the pump chamber 112C and/or the wall 112D, preferably in portions and/or temporarily, in particular by means of the pump 260.

The pump apparatus 112, in particular its pump chamber 112C, preferably comprises an inlet opening or inlet 112A and an outlet opening or outlet 112B and/or is preferably fluidically connected to an inlet channel 114B and an outlet channel 114C of the fluid system 103, preferably by means of the inlet or inlet opening 112A and the outlet or outlet opening 112B, respectively.

The inlet 112A is preferably arranged on a first end of the pump chamber 112C and the outlet 112B is preferably arranged on a second end of the pump chamber 112C.

Preferably, the conveying direction of the pump apparatus 112 can be reversed. Depending on the operation of the pump apparatus 112, the inlet 112A can be used as the outlet, at least temporarily, and the outlet 112B can be used as the inlet, at least temporarily.

In the present embodiment, the cartridge 100 comprises just one single pump apparatus 112. However, constructional solutions are possible as well, in which the cartridge 100 comprises a plurality of pump apparatuses 112 and/or pump chambers 112C.

Due to the pump apparatus 112 and/or pump chamber 112C, it is possible to test the sample, to convey the sample, reagents, gas and/or other fluids, to mix the sample with reagents and/or to treat the sample in another way. In particular, it is possible to control the (dynamic) pressure and/or speed of the fluid, in particular of the sample and/or reagents, through all the cavities, channels and valves.

Once the receiving cavity 104 has been closed, in particular after the sample has been introduced in the cartridge 100, the fluid system 103 forms, in particular together with the receiving cavity 104 and/or the connected cavities 105 to 111, the channels 114, the pump apparatus 112 and/or the sensor apparatus 113, a closed circuit for fluids, in particular gas, air and/or liquids.

Once the sample has been introduced into the cartridge 100, in particular its receiving cavity 104, and the cartridge 100 has been closed, the cartridge 100 can be inserted into and/or received by the analyzer 200 in order to test the sample. Alternatively, the sample could also be introduced into the cartridge 100 after being received by the analyzer 200.

The analyzer 200 preferably comprises a receptacle 201, a housing 212, an access cover or housing part 212B and/or an opening 213.

Preferably, the analyzer 200, in particular its housing 212, can be opened by moving the access cover/housing part 212B relative to the housing 212 and/or such that the opening 213 is formed and/or the receptacle 201 is accessible, mostly preferred from the top.

Preferably, the receptacle 201 is adapted to receive the cartridge 100.

FIG. 1 shows the analyzer 200 in the opened state, i.e. when the receptacle 201 is accessible and/or the opening 213 is formed. Here, the cartridge 100 has already been inserted into the analyzer 200, preferably through the opening 213 into the receptacle 201.

FIG. 1 shows the analyzer 200 still in the open position, i.e. wherein the access cover/housing part 212B has not been closed yet. However, for the test it is necessary to close the analyzer 200.

The analyzer 200 preferably comprises a drive apparatus 233 and/or the pump 260, preferably wherein the drive apparatus 233 and/or the pump 260 are/is arranged within the (common) housing 212.

Preferably, the drive apparatus 233 is adapted to position and/or clamp the cartridge 100 within the analyzer 200. In particular, the drive apparatus 233 is adapted to move the cartridge 100 and the pump 260 relative to one another.

In particular, the drive apparatus 233 is adapted to push/press the cartridge 100 against the pump 260, in particular such that the cartridge 100, mostly preferred its pump apparatus 112, comes into contact with the pump 260.

Preferably, the cartridge 100 is arranged between the drive apparatus 233 and the pump 260. Mostly preferred, the drive apparatus 233 faces the front 100A of the cartridge 100 and the pump 260 faces the back 100B of the cartridge 100.

With other words, the drive apparatus 233 and the pump 260 preferably act on different sides of the cartridge 100. However, constructional solutions are also possible, wherein the drive apparatus 233 and the pump 260 are arranged on the same side of the cartridge 100 and/or wherein the drive apparatus 233 is adapted to pull the cartridge against the pump 260.

The drive apparatus 233 preferably comprises a drive 233A, a rod 233D and a drive head 233E, preferably wherein the drive head 233E is—directly or indirectly—connected/connectable to the cartridge 100, in particular its front 100A, mostly preferred at a center thereof.

Preferably, the drive apparatus 233 is embodied as a stepping motor, in particular having a threaded spindle as a rod 233D. However, other constructional solutions are possible as well, e.g. wherein the drive apparatus 233 comprises a gear-mechanism and/or is pneumatically operated.

According to another, preferred embodiment (not shown) the pump 260 is moved or movable towards the cartridge 100, which might be immovably held once being inserted in the analyzer 200. It is also possible, that both, the pump 260 and the cartridge 100 are moved towards each other.

FIG. 4 shows the back 100B of the cartridge 100 together with the pump 260, both being in contact with each other.

As already mentioned, the pump 260 is preferably adapted to (mechanically) act on the cartridge 100, in particular its pump apparatus 112, preferably such that the sample and/or any other fluid can be conveyed through the cartridge 100, the pump apparatus 112 and/or the pump chamber 112C. Mostly preferred, the pump 260 is—directly and/or concentrically—placed on the pump apparatus 112 and/or its pump chamber 112C.

The pump 260 preferably comprises a motor 261, pump head 262 and/or a coupling apparatus 263, preferably wherein the pump head 262 is (mechanically) connected to the motor 261 via the coupling apparatus 263 and/or wherein the coupling apparatus 263 is adapted to transmit a torque from the motor 261 to the pump head 262, in particular such that the pump head 262 rotates.

Preferably, the pump head 262 can be rotated about a central/rotational axis AC and/or a motor axis AM, in particular by means of the motor 261, as indicated by arrows in FIG. 4.

The motor axis AM is preferably defined by the motor 261, in particular its shaft.

The central/rotational axis AC is preferably defined by the pump head 262, in particular the axis around which the pump head 262 rotates or is rotatable.

Preferably, the central/rotational axis AC of the pump head 262 (normally) corresponds to or is aligned with the motor axis AM. However, the central axis AC and the motor axis AM might be offset or misaligned to one another, as will be described later, in particular with reference to FIGS. 9 and 10.

The central axis AC and/or the motor axis AM preferably run/runs through the pump 260 and/or form/forms a center/longitudinal axis of the—preferably longitudinal and/or partially cylindrical—pump 260.

When being in contact with the cartridge 100, in particular its pump apparatus 112, the central axis AC and/or the motor axis AM are/is preferably arranged as at least essentially perpendicular to the cartridge 100 and/or its main plane and/or is concentrical to the preferably arcuate pump chamber 112C.

In the following, the construction of the pump 260, in particular its pump head 262, will be described with reference to the FIGS. 5 to 10.

Figure 5:
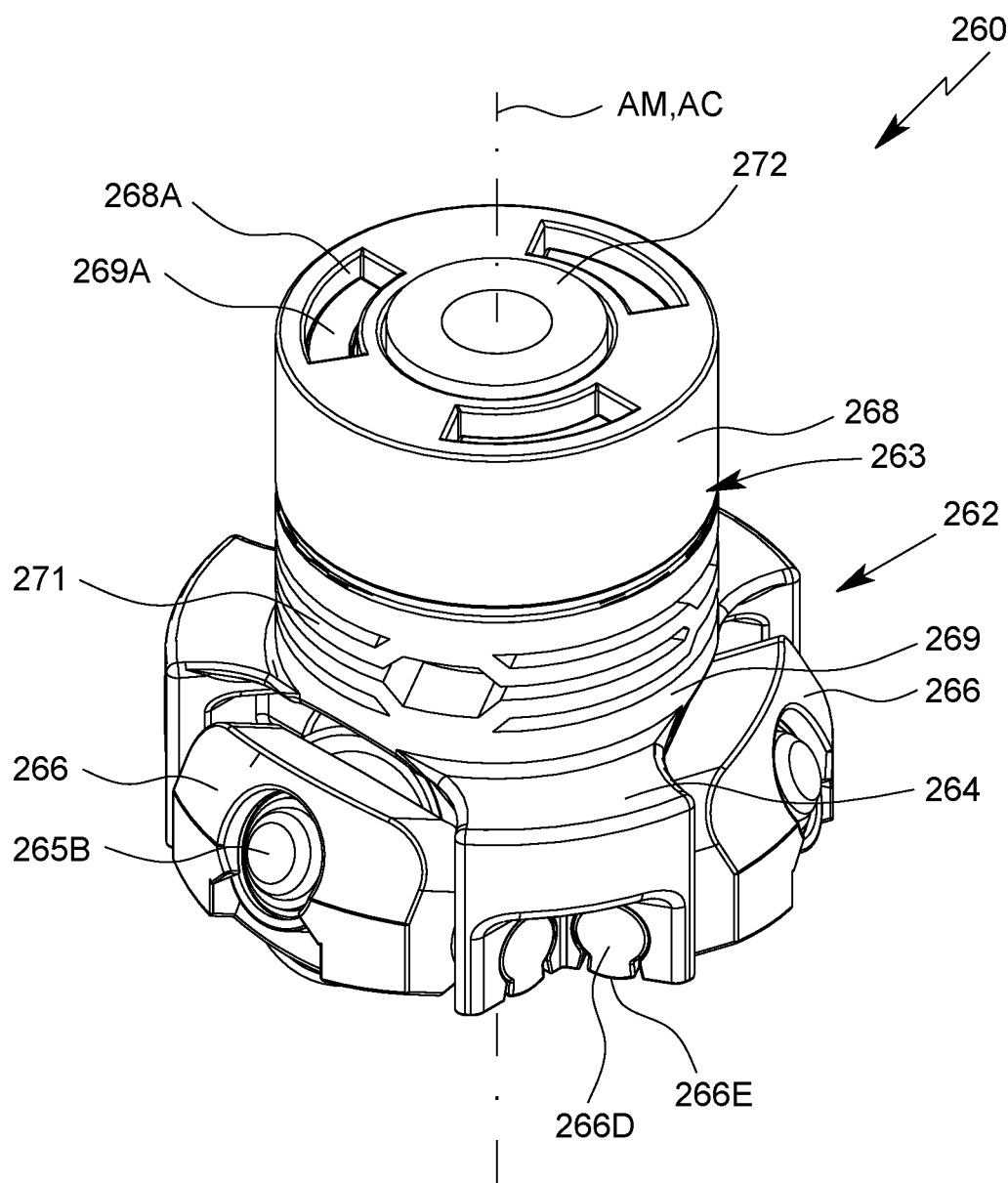
FIG. 5 is a perspective view of the pump head at an angle from above.
Figure 6:
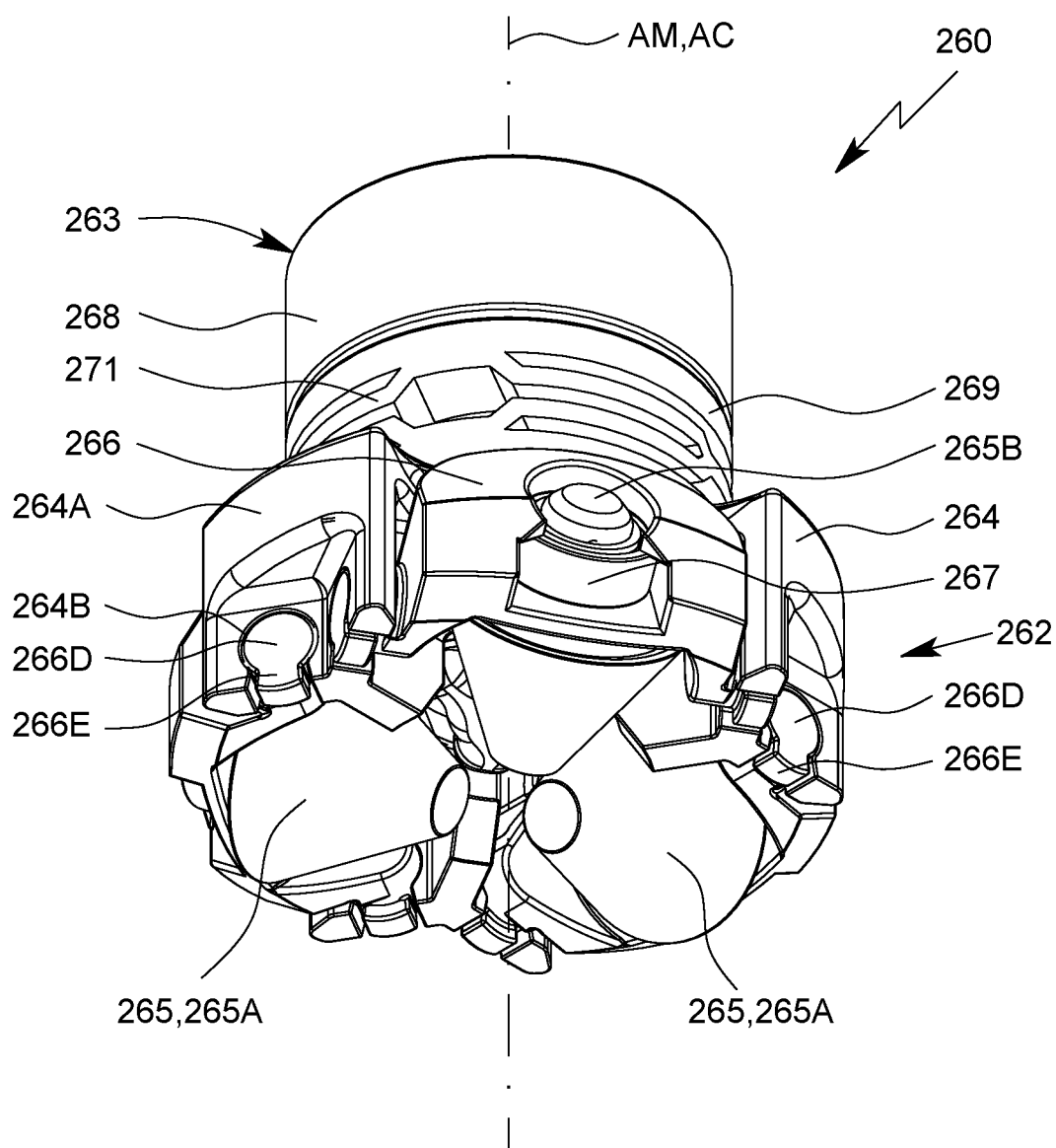
FIG. 6 is a perspective view of the pump head at an angle from below.
Figure 7:
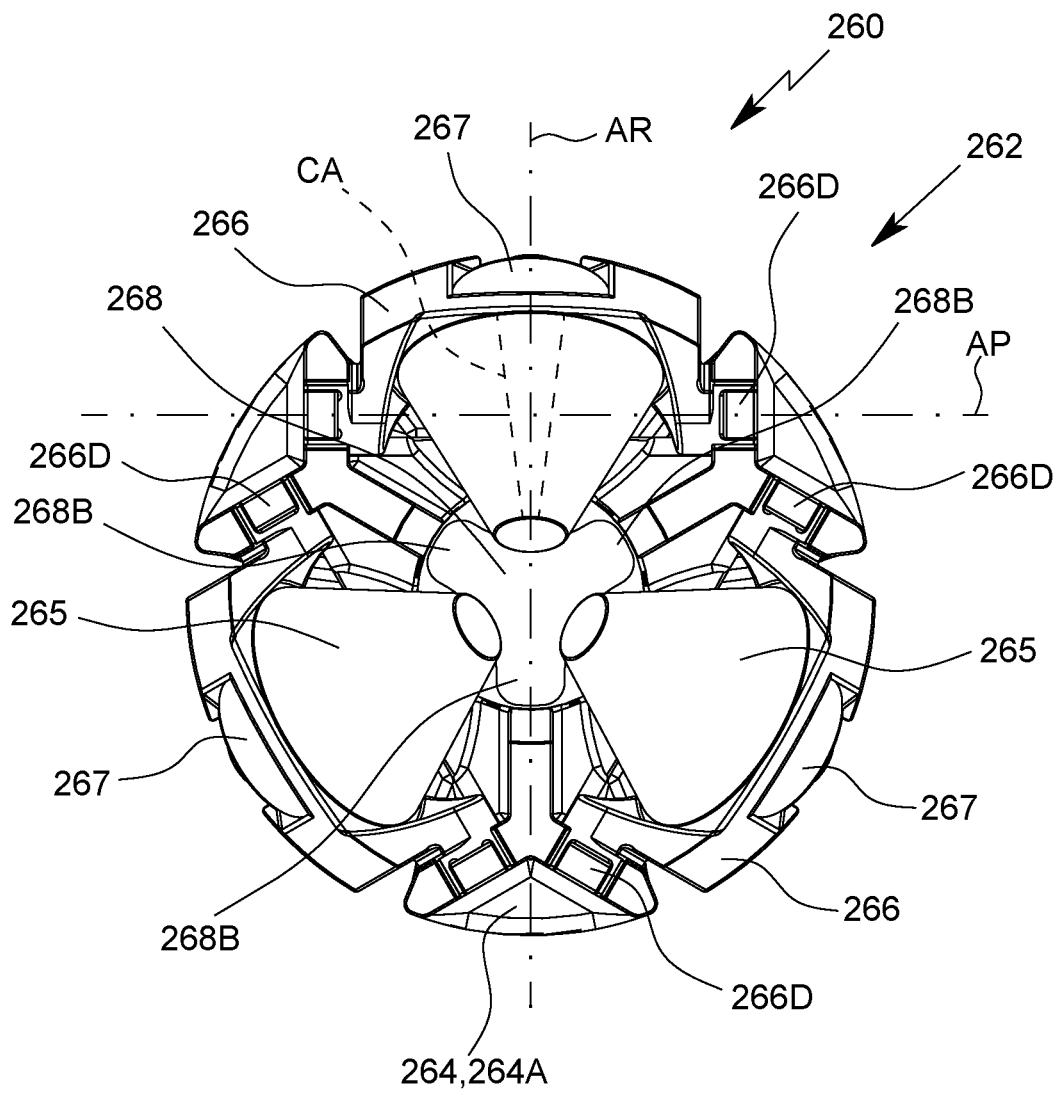
FIG. 7 is a schematic view of the front side of the pump showing its preferably cone-shaped rollers.
Figure 8:
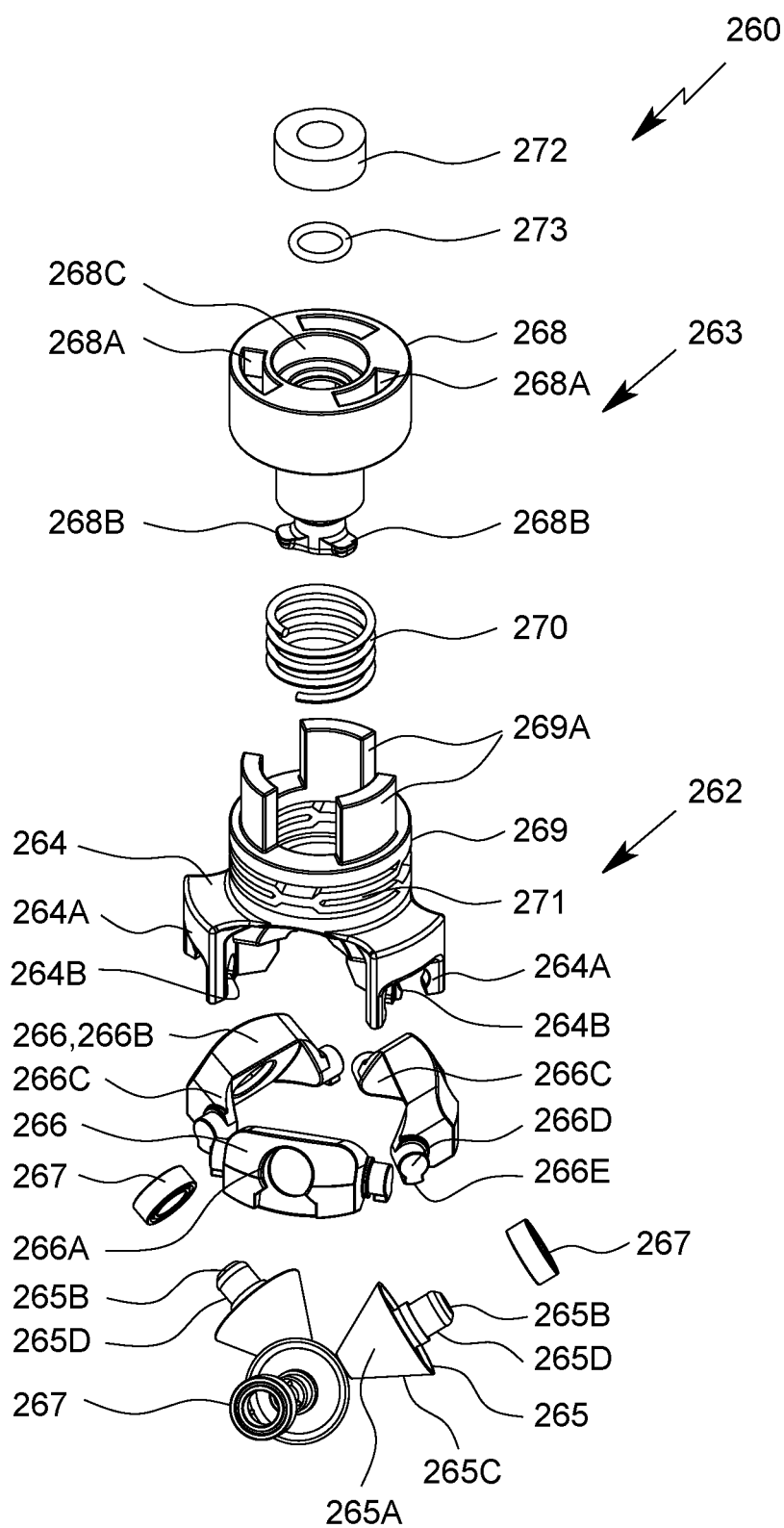
FIG. 8 is an exploded view of the pump.

FIGS. 5 to 7 show the pump 260 in different perspective views. FIG. 8 is an exploded view of the pump 260. FIGS. 9 and 10 show a schematic section of the pump 260 when being in contact with the cartridge 100.

The pump 260, in particular its pump head 262, preferably comprises a main body 264, a plurality of rollers 265 for contacting the cartridge 100, in particular its pump apparatus 112, and/or a plurality of brackets 266 for the rollers 265, preferably wherein the rollers 265 and the brackets 266 are evenly spaced around the circumference of the preferably at least essentially cylindrical pump head 262.

In the embodiment shown in the FIGS. 5 to 10, the pump 260, in particular its pump head 262, comprises three rollers 265 and three corresponding brackets 266. However, the pump 260 might be equipped with a different number of rollers 265 and brackets 266.

Preferably, the rollers 265 are cone-shaped and/or constructed as truncated cones, preferably wherein each roller 265 comprises a cone angle of more than 45° and/or less than 90°, in particular of about 60°.

Mostly preferred, the rollers 265 are adapted to compress the pump chamber 112C and/or wall 112D of the pump apparatus 112, preferably partially and/or in order to convey the sample or a fluid contained therein, as already mentioned.

In particular, the rollers 265 roll over the pump apparatus 112, preferably the pump chamber 112C and/or the wall 112D, and/or along a circular path and/or a radius that corresponds to the circular path and/or the radius of the pump apparatus 112, in particular the pump chamber 112C and/or wall 122D.

Preferably, each roller 265 defines/comprises an associated roller axis AR as shown in FIGS. 7 to 10, preferably wherein each roller 265 can rotate about its roller axis AR and/or wherein each roller axis AR forms a rotational/symmetry axis of its associated roller 265.

Each roller 265 is preferably rotatably mounted to the pump head 262, in particular to one of the brackets 266.

Preferably, the roller axes AR intersect with the central axis AC, the motor axis AM and/or the center of the (arc-shaped) pump apparatus 112, in particular in the main plane of the pump apparatus 112 and/or cartridge 100. With other words, the center of the circle the rollers 265 roll along corresponds to the circle center of the pump apparatus 112.

Preferably, the angle enclosed by the central axis AC/motor axis AM and the roller axis AR is more than 30° or 45° and/or less than 80°, mostly preferred of about 60°.

Preferably, the angle enclosed by the cartridge 100 or its surface and the roller axis AR is more than 20° and/or less than 60°, mostly preferred of about 30°.

Mostly preferred, the angle enclosed by the central axis AC/motor axis AM and the roller axis AR can vary, at least in a limited ranged and/or due to the brackets 266, as will be described in the following.

Each roller 265 is preferably formed integrally and/or in one piece.

Each roller 265 is preferably mushroom-shaped and/or preferably comprises a cone-shaped roller head 265A and a preferably cylindrical roller shaft 265B, preferably wherein the respective roller head 265A comprises or forms a free end of the roller 265 and/or the respective shaft 265B comprises or forms a fixed end of the roller 265.

The roller heads 265A and/or the free ends of the rollers 265 are preferably turned towards the central axis AC/motor axis AM and/or the center of the pump 260. The roller shafts 265B and/or the fixed ends are preferably turned away from the central axis AC/motor axis AM and/or the center of the pump 260. With other words, the rollers 265 preferably point inwards and/or towards the central axis AC/motor axis AM and/or the central axis of the pump 260.

Preferably, each roller head 265A comprises or forms a contact surface 265C, preferably wherein the contact surface 265C is adapted to act on and/or contact the cartridge 100, in particular its pump apparatus 112 or the pump chamber 112C thereof, when the pump 260 engages the cartridge 100.

Preferably, the rollers 265 extend over the entire (radial) width and/or the radial extension of the pump apparatus 112 or the pump chamber 112C thereof.

The contact surface 265C preferably comprises a length and/or radial extension that is at least as large as the (radial) width and/or radial extension of the pump apparatus 112 or the pump chamber 112C thereof, in particular so that the rollers 265 radially extend over the pump apparatus 112 or the pump chamber 112C thereof.

Preferably, the pump 260, in particular the pump head 262, comprises a plurality of roller bearings 267, preferably wherein the rollers 265 are mounted to the pump head 262 and/or the corresponding brackets 266 (each) via a roller bearing 267. However, other constructional solutions are also possible, wherein the rollers 265 are directly mounted to the pump head 262 and/or the corresponding brackets 266.

Due to the roller bearings 267, the friction between the rollers 265 and the bracket 266 is reduced and the rollers 265 can run smoothly.

As best seen in FIGS. 8 to 10, each roller 265, in particular its roller shaft 265B, preferably comprises or forms a bearing surface 265D for the roller bearings 267.

Preferably, each roller bearing 267 is (directly) clipped on a corresponding roller 265, in particular its roller shaft 265B, mostly preferred by (temporarily) deforming the roller shaft 265B and/or a annular protrusion thereof.

Preferably, each bracket 266 comprises a receptacle 266A for receiving a corresponding roller bearing 267.

Each receptacle 266A is preferably embodied as a pocket and/or radially open, in particular such that a corresponding roller bearing 267 can be inserted, mostly preferred clipped, into the receptacle/pocket 266A, in particular radially to the roller axis AR and/or by (temporarily) deforming the receptacle 266A and/or a wall thereof and/or such that each roller bearing 267 is held within the corresponding receptacle 266A in a form-fitting manner.

The brackets 266 are preferably adapted to hold the rollers 265 and/or to connect the rollers 265 to the main body 262, mostly preferred in a pivotable manner.

Each bracket 266 is preferably formed integrally and/or as one piece.

Each bracket 266 is preferably at least essentially U-shaped and/or comprises a central portion 266B and two side portions 266C.

Preferably, the central portion 266B comprises or forms the receptacle 266A for the corresponding roller 265 and/or roller bearing 267.

Preferably, the side portions 266C flank the central portion 266B and/or are arranged at least essentially perpendicular to the central portion 266B.

Each bracket 266 is pivotably mounted to the main body 264 and/or can be pivoted relative to the main body 264, in particular such that the orientation of the rollers 265 and/or the roller axes AR is adaptable and/or the angle enclosed by the roller axis AR and the central axis AC/motor axis AM can vary depending on the movement of the brackets 266 relative to the main body 264.

Preferably, the pump 262 comprises a plurality of pivot axes AP, preferably wherein each roller 265 is pivotable about a corresponding pivot axis AP. Mostly preferred, each bracket 266 comprises a pivot axis AP, preferably wherein the respective pivot axes AP run through the associated side portions 266C of the brackets 266.

Mostly preferred, pivot axes AP are spaced apart from the central axis AC/motor axis AM.

In particular, the pivot axes AP lie in a common plane, preferably wherein the plane defended by the pivot axes AP is arranged perpendicular to the central axis AC/motor axis AM.

As best seen in FIG. 7, the pivot axes AP preferably run through the respective rollers 265 and/or intersect with the respective roller axes AR, mostly preferred at a right angle. In this way, an unwanted tilting/lifting of the rollers 265 is prevented, in particular when pressing the pump head 262 against the cartridge 100 or vice versa. Further, the force of the pump head 262 is exerted in a more precise and direct manner on the cartridge 100.

Preferably, the pivot axes AP intersect with the roller axes AR at a level between ¼ and ⅓ of the height of the rollers 265, measured from its broader bottom (compared to its narrower top). This allows an at least essentially constant pressure distribution along the roller axes AR, the contact surface 265C and/or over the width and/or radial extension of the pump apparatus 112 or its pump chamber 112D as the cartridge 100 might bend (locally) when brought into contact with the pump head 262.

Due to the shape of the rollers 265, the radius of the rollers 265 varies along the roller axes AR thereof. As the cartridge 100, in particular the pump apparatus 112 and/or its pump chamber 112D, is flexible, also the contact area CA increases/broadens with an increasing radius of the rollers 265 and/or along the roller axes AR, as indicated by dashed lines in FIG. 7. Thus, by arranging the pivot axes AP outside the center of the rollers 265, in particular within the broader bottom of the rollers 265, the pressure exerted by the pump 260 or its rollers 265 on the cartridge 100 is at least essentially constant and/or distributed more evenly along the contact surface 265C of the rollers 265 and/or the width and/or radial extension of the pump apparatus 112 or its pump chamber 112D.

Preferably, the pump 262, in particular the main body 264 or each bracket 266, comprises or forms a plurality, in particular a pair, of pivots 266D, preferably wherein a pair of pivots 266D defines a pivot axis AP and/or is concentrical to the associated pivot axis AP.

The pivots 266D are preferably embodied as protrusions or pins that extend at least essentially perpendicular to the side portions 266C and/or at least essentially parallel to the central portion 266B. However, constructional solutions are also possible, wherein the main body 264 comprises or forms the pivots 266D.

Preferably, for each bracket 266, the respective pivots 266D are arranged coaxially towards each other and/or comprise or form a common pivot axis AP.

The main body 264 is preferably adapted to hold the plurality of brackets 266, preferably in a pivotable manner.

Preferably, the main body 264 comprises or forms a plurality of holders 264A, in the present embodiment three holders 264A, that are adapted to hold the respective brackets 266.

The main body 264, in particular each holder 264A, preferably comprises a plurality of sockets 264B, preferably wherein each socket 264B is adapted to receive a corresponding pivot 266D and/or wherein each pivot 266D is (directly) clipped in one corresponding socket 264B, in particular by (temporarily) deforming the socket 264B and/or a wall thereof and/or such that the pivot 266D is held within the socket 264B in a form-fitting manner.

Preferably, the sockets 264B are open radially to the corresponding pivot axis AP, in particular such that the brackets 266 can be clipped in the main body 264 and/or the corresponding socket 264B from the side of the pump head 262 facing the cartridge 100.

Optionally, the main body 264, preferably each bracket 266, comprises or forms a stop 266E limiting the pivot movement of the brackets 266 and/or rollers 265.

In the embodiment shown in the FIGS. 5 to 10, each pivot 266B comprises or forms a stop 266E, preferably wherein each stop 266E is constructed as a protrusion that extends radially to the pivot axis AP and/or contacts the corresponding holder 264A when a maximum pivot movement is reached.

As already mentioned, the rollers 265 can pivot about the respective pivot axes AP, preferably by at least 0.5° or 1° and/or by at most 10° or 8°.

With other words, the angle enclosed by the central axis AC/motor axis AM and the pivot axes AP and/or enclosed by the cartridge 100 or its surface and the pivot axes AP can vary and/or be adapted by at least 0.5° or 1° and/or by at most 10° or 8°. The variation of the angle is preferably limited due to the stops 266E.

Preferably, the pump 260, in particular the pump head 262, is constructed as a screwless assembly and/or is mounted without using screws.

As best seen in FIG. 8, all parts of the pump head 262 are preferably connected to one another in a screwless manner and/or by snapping/clipping.

Preferably in a first assembly step, the optional roller bearings 267 are—in particular directly—snapped/clipped in the brackets 266, in particular the receptacles 266A, mostly preferred such that the roller bearings 267 are held within the brackets 266 in a form-fitting and/or screwless manner.

The rollers 265, in particular the roller shafts 265B, are preferably (subsequently) snapped/clipped in the brackets 266, in particular the receptacles 266A, and/or the optional roller bearings 267 contained therein, preferably in a second assembly step, mostly preferred such that the rollers 265 are attached to the brackets 266 in a form-fitting and/or screwless manner and/or by means of the roller bearings 267.

Preferably, the brackets 266, in particular the pivots 266D, are—in particular directly—snapped/clipped in the main body 264, in particular the sockets 264B, preferably in a third assembly step, mostly preferred such that the pivots 266D are held within the sockets 264B in a form-fitting and/or screwless manner.

Preferably, the pump head 262 is plugged on the motor 261, in particular its shaft, preferably in a fourth assembly step.

Thus, the assembly of the pump head 262 can be done without using screws or any kind of tools. In this way, an easy and fast assembly of the pump 260, in particular its pump head 262, is possible.

As already mentioned, the pump 260 preferably comprises a coupling apparatus 263, preferably wherein the pump head 262 is connected to the motor 261 via the coupling apparatus 263.

The coupling apparatus 263 is preferably adapted to transmit a torque from the motor 261, in particular its shaft, to the pump head 262.

The coupling apparatus 263 is preferably constructed as a bayonet coupling and/or a beam coupling, as will be described in the following in particular with reference to FIGS. 8 to 10.

The coupling apparatus 263 is preferably of multiple-part construction.

The coupling apparatus 263 preferably comprises a first coupling part 268 and a second coupling part 269, preferably wherein the coupling parts 268, 269 are connected to one another via a bayonet joint and/or in a detachable manner.

The first coupling part 268 is preferably (directly) connected to the motor 261, in particular its shaft, and the second coupling part 269 is preferably (directly) connected to the pump head 262.

In the shown embodiment, the second coupling part 269 and the pump head 262 are preferably formed integrally and/or as one piece. However, constructional solutions are possible as well, wherein the second coupling part 269 is connected to the pump head 262 in a force-fitting and/or a form-fitting manner and/or by welding.

Preferably, the coupling parts 268, 269 are interlocked with each other and/or secured to one another, in particular in a form-fitting and/or force-fitting manner, mostly preferred in a circumferential direction and in an axial direction.

Preferably, the first coupling part 268 comprises at least one coupling socket 268A and the second coupling part 269 comprises at least one corresponding coupling rod 269A, preferably wherein the coupling rod 269A is inserted into the coupling socket 268A, in particular such that a torque can be transmitted between the coupling parts 268, 269 and/or in order to circumferentially connect the coupling parts 268, 269 in a form-fitting manner.

Mostly preferred, the coupling rod 269A is embodied as an axial protrusion, preferably wherein the protrusion extends into the coupling socket 268A.

Preferably, the coupling socket 268A is embodied as an axial recess/cutout.

Preferably, the shape/contour of the coupling socket 268A corresponds/matches the shape/contour of the coupling rod 269A.

Preferably, the coupling rod 269A is radially and/or circumferentially held in the coupling socket 268A, in particular in order to transmit a torque from the first coupling part 268 to the second coupling part 269.

With other words, by means of the coupling rod 269A and the coupling socket 268A, in particular by inserting the coupling rod 269A into the coupling socket 268A, the coupling apparatus 263 is preferably secured against twisting and/or a rotation of the first coupling part 268 relative to the second coupling part 269 is prevented or limited.

It is preferred, that the coupling rod 269A is axially movable relative to the coupling socket 268A, in particular to provide an axial play and/or for the assembly/disassembly of the pump 260, in particular the pump head 262, as will be explained later.

In the present embodiment, the coupling apparatus 263 comprises multiple, here three, coupling sockets 268A and corresponding coupling rods 269A. However, a single coupling socket 268A and a single coupling rod 269A would be sufficient to provide a torque transmission between the coupling parts 268, 269.

The first coupling part 268 preferably comprises at least one radial protrusion 268B, preferably wherein the radial protrusion 268B is inserted into a corresponding recess of the second coupling part 269 and/or (radially) engages in the second coupling part 269, in particular in order to connect the coupling parts 268, 269 axially in a form-fitting manner.

With other words, by means of the radial protrusion 268B the coupling apparatus 263 is preferably secured against (accidental) decoupling of the first coupling part 268 and the second coupling part 269.

In the present embodiment, the first coupling part 268 comprises several, here three, radial protrusions 268B (radially) engaging in the second coupling part 269.

Mostly preferred, the radial protrusions 268B form a (star-shaped) head of the first coupling part 268, preferably wherein the head is inserted into a correspondingly (star-shaped) recess of the second coupling part 269.

By inserting the first coupling part 268 in the second coupling part 269 and subsequently turning/twisting the first coupling part 268 and the second coupling part 269 relative to one another, the radial protrusion 268B engages in the second coupling part 269 and/or the coupling rod 269A engages in the coupling socket 268A, in particular such that an interlocked connection and, thus, a bayonet joint is established.

In the context of the present invention, the term "bayonet" preferably means a mechanical connection/coupling/joint between two parts, here the coupling parts 268, 269, wherein the connection is established by a combination of a translational motion and a rotational motion between the two parts, in particular such that the parts are (rigidly) attached to one another and secured against an unwanted disassembly or release.

The pump 260, in particular the pump head 262, mostly preferred the coupling apparatus 263, is preferable flexible, tiltable, bendable, compressible and/or adapted to compensate a—preferably angular—misalignment and/or an offset between the pump head 262 and the motor 261 and/or between the first coupling part 268 and the second coupling part 269 and/or to absorb vibrations caused by the motor 261.

Mostly preferred, the central/rotational axis AC of the pump head 262 can be misaligned/tilted/offset relative to the preferably fixed motor axis AM of the motor 261, in particular due to the flexible pump head 262 or due to the flexible coupling apparatus 263.

The pump 260, in particular the coupling apparatus 263, preferably comprises an inner/coupling spring 270, preferably wherein the inner spring 270 is arranged within the coupling apparatus 263 and/or presses against the first coupling part 268 and the second coupling part 269.

Preferably, the inner spring 270 is pretensioned, in particular such that the pump head 262 can only be compressed and/or the coupling parts 268, 269 can only be moved axially relative to one another against a spring force and/or by compressing the inner spring 270.

Preferably, the second coupling part 269 surrounds the inner spring 270. However, other constructional solutions are possible as well. In particular, it is also possible that the inner spring 270 surrounds the first coupling part 268 and/or the second coupling part 269.

The pump 260, in particular its pump head 262 or coupling apparatus 263, is preferably compressible, in particular by axially moving the first coupling part 268 and the second coupling part 269 relative to one another and/or by compressing the inner spring 270.

Preferably, the pump 260, in particular the pump head 262, mostly preferred the coupling apparatus 263, is compressed when the cartridge 100 is pushed against the pump 260 or vice versa, in particular by at least 1 mm and/or at most 10 mm and/or by compressing the inner spring 270. In this way, a force of preferably more than 10 N or 20 N and/or less than 100 N or 50 N is exerted on the cartridge 100, in particular its pump apparatus 112, by means of the pump 260.

By compressing the pump 260, in particular its pump head 262 or coupling apparatus 263, the coupling rod 269A is pushed (further) into the (corresponding) coupling socket 268A, mostly preferred until a further movement is prevented, e.g. by means of a stop.

Thus, an unwanted/accidental decoupling of the coupling parts 268, 269 during operation and/or when the cartridge 100 is pressed against the pump head 262 (or vice versa) is prevented as the coupling parts 268, 269 are secured against twisting due to the connection of the coupling rod 269A and the coupling socket 268A (even though the radial protrusion 268B is preferably lifted when compressing the pump 260).

Preferably, only by disconnecting the coupling rod 269A and the coupling socket 268A from each other, in particular by pulling the coupling rod 269A out of the coupling socket 268A, the coupling parts 268, 269 can be rotated relative to one another, in particular such that an axial disconnection is possible and/or such that the radial protrusion 268B does not engages into the second coupling part 269 and/or overlaps the recesses and can be pulled out.

With other words, preferably (only) the second coupling part 269 is to be compressed, in particular until it does not axially engage into the first coupling part 268 by means of the coupling rod 269A and/or until the coupling rod 269A is completely pulled out of the coupling socket 268A, in order to rotate the coupling parts 268, 269 relative to one another and/or (subsequently) decouple the coupling parts 268, 269 from one another.

The pump 260, in particular the coupling apparatus 263, mostly preferred the second coupling part 269, is preferably at least partially flexible/compressible and/or preferably forms or comprises an outer/beam/tumbling spring 271, preferably wherein the outer spring 271 allows a (further) compression and/or tumbling motion of the pump head 262 and/or of the second coupling part 269, in particular relative to the motor 261 and/or the first coupling part 268 and/or even in the compressed state of the inner spring 270.

The outer spring 271 is preferably formed integrally with the coupling apparatus 263, in particular the second coupling part 269. Mostly preferred, the outer spring 271 is formed by the wall of the second coupling part 269.

Preferably, the outer spring 271 is formed by gaps, notches, cutouts, cavities or the like within the coupling apparatus 263, in particular the second coupling part 269 and/or its wall.

In the present embodiment, the outer spring 271 is formed by a plurality of webs that connect the main body 264 with the coupling rods 269A.

In this way, the coupling apparatus 263, in particular the second coupling part 269, is made flexible/compressible and/or capable of elastically yielding.

Preferably, due to the outer spring 271 and/or the compression thereof, the coupling apparatus 263 can be assembled or disassembled. In particular, the second coupling part 271 can be compressed (without compressing the inner spring 270) such that the coupling rod 269A is completely pulled out of the coupling socket 268A and/or the coupling parts 268, 269 can be rotated relative to one another in order to (subsequently) decouple the coupling parts 268, 269 from one another.

Further, due to the outer spring 271 it is possible to compensate angular misalignment between the motor axis AM and the central axis AC.

Preferably, the coupling apparatus 263 comprises an axial play, preferably of more than 1 mm and/or less than 10 mm, in particular such that the first coupling part 268 and the second coupling part 269 can axially move relative to one another, in particular only by compressing the inner spring 270 and/or without compressing the outer spring 271, at least until the first coupling part 268 comes (axially) into direct contact with the second coupling part 269. Preferably, a further compression of the pump head 262 takes place by compressing both, the inner spring 270 and the outer spring 271.

Preferably, the spring constant of the outer spring 271 differs from the spring constant of the inner spring 270. Mostly preferred, the outer spring 271 is harder than the inner spring 270.

FIG. 10 shows the pump head 262 when being deflected, e.g. when the motor axis AM does not correspond to the central axis AC and/or when the motor axis AM is not perpendicular to the main plane of the cartridge 100.

Due to the construction as a beam coupling and/or due to the spring(s) 270, 271, the pump head 262, in particular the second coupling part 269, can bend/tilt according to the alignment of the cartridge 100 relative to the pump 260, in particular its motor axis AM. In this way, it is possible to compensate an angular misalignment between the cartridge 100 and the motor 261, i.e. when the cartridge 100 is not perpendicularly arranged to the motor axis AM.

In particular, during operation, the central/rotational axis AC of the pump head 262 can be kept perpendicular to the main plane of the cartridge 100 due to the construction as a beam coupling and/or the outer spring 271 and/or bending/tilting of the pump head 262 or second coupling part 269.

The pump 260 preferably comprises an axial bearing 272, preferably wherein the motor 261, in particular its housing, and the pump head 262, in particular the coupling apparatus 263, mostly preferred the first coupling part 268, are axially connected to one another via the axial bearing 272.

Preferably, the axial bearing 272 is adapted to (directly) transmit an axial force of the pump head 262, e.g. introduced via the cartridge 100 that is pressed against the pump head 262, to the housing of the motor 261. In this way the shaft of the motor 261 is not axially loaded.

The coupling apparatus 263, in particular the first coupling part 268, comprises preferably a central recess 268C, wherein the shaft of the motor 261 and/or the axial bearing 272 can be introduced into the central recess 268C.

Preferably, the axial bearing 272 is secured against slip-off by an optional securing ring 273.

In order to transmit a torque from the motor 261 to the pump head 262, the coupling apparatus 263, in particular the first coupling part 268, is preferably connected to the motor 261, in particular its shaft, in a form-fitting manner, at least in the direction of rotation.

For a torque transmission the shaft of the motor 261 and the recess 268C preferably are not circular, but might comprise an angular or oval cross-section, for example.

Individual aspects and features of the present invention may be implemented independently from another, but also in any desired combination.

In particular, the present invention relates also to any one of the following aspects which can be realized independently or in any combination, also in combination with any aspects described above or in the claims:

1. A peristaltic pump 260 for conveying a fluid within a cartridge 100,
   wherein the pump 260 comprises a motor 261 and a pump head 262 that can be rotated about a central axis AC by means of the motor 261,
   wherein the pump head 262 comprises a main body 264, a plurality of preferably cone-shaped rollers 265 for contacting the cartridge 100 and a plurality of brackets 266 for the rollers 265,
   wherein each of the rollers 265 is mounted to one of the brackets 266 and can be rotated about a roller axis AR, and
   wherein each of the brackets 266 is mounted to the main body and can be pivoted about a pivot axis AP relative to the main body 264, characterized
   in that the pump head 262 is constructed as a screwless assembly and/or that the rollers 265 are clipped in the brackets 266 and the brackets 266 are clipped in the main body 264, and/or in that the pump 260 comprises a coupling apparatus 263 for connecting the pump head 262 to the motor 261, wherein the coupling apparatus 263 is constructed as a bayonet and/or beam coupling, and/or in that each pivot axis AP runs through the associated roller 265.

2. The pump according to aspect 1, characterized in that each of the rollers 265 comprises a free end that is turned towards the central axis AC.

3. The pump according to aspect 1 or 2, characterized in that each of the rollers (265) comprises a bearing surface 265D and in that the pump 260 comprises a plurality of roller bearings 267.

4. The pump according to aspect 3, characterized in that each of the roller bearings 267 is clipped on one of the bearing surfaces 265D.

5. The pump according to aspect 3 or 4, characterized in that each of the brackets 266 comprises a receptacle 266A for receiving one of the roller bearings 267 and/or in that each of the roller bearings 267 is clipped in one of the brackets 266, preferably radially to the pivot axis AP.

6. The pump according to any of the preceding aspects, characterized in that each of the brackets 266 comprises a pair of pivots 266D, wherein each pair of pivots 266D define one pivot axis AP.

7. The pump according to aspect 6, characterized in that the main body 264 forms or comprises a plurality of sockets 264B, wherein each of the sockets 264B is adapted to pivotably receive one of the pivots 266D and/or wherein each of the pivots 266D is clipped in one of the sockets 264B.

8. The pump according to aspect 6 or 7, characterized in that each of the pivots 266D comprises or forms a stop 266E limiting the pivoting movement of the rollers 265.

9. The pump according to any of the preceding aspects, characterized in that the coupling apparatus 263 is at least partially flexible and/or adapted to compensate misalignment and/or an offset between the pump head 262 and the motor 261.

10. The pump according to any of the preceding aspects, characterized in that the coupling apparatus 263 comprises an outer spring 271 for a tumbling motion of the pump head 262 and/or an inner spring 270 for an axial motion of the pump head 262.

11. The pump according to aspect 10, characterized in that the outer spring 271 is embodied as an integrated spring and/or formed by the wall of the coupling apparatus 263.

12. The pump according to any of the preceding aspects, characterized in that the coupling apparatus 263 comprises a first coupling part 268 and a second coupling part 269, preferably wherein the coupling parts 268, 269 are connected to one another via a bayonet joint and/or in a detachable manner and/or wherein the coupling parts 268, 269 are pressed apart by the inner spring 270.

13. The pump according to aspect 12, characterized in that the first coupling part 268 comprises at least one radial protrusion 268B engaging in the second coupling part 269 for an axial coupling of the coupling parts 268, 269 and/or in that the second coupling part 269 comprises at least one coupling rod 269A engaging in the first coupling part 268 for a torque transmission between the coupling parts 268, 269.

14. The pump according to any of the preceding aspects, characterized in that the pump 260 comprises an axial bearing 272, wherein the motor 261, in particular its housing, and the coupling apparatus 263, in particular its first coupling part 268, are axially connected to one another via the axial bearing 272.

15. Analyzer 200 for testing an in particular biological sample, the analyzer 200 comprising a receptacle 201 for a cartridge 100 containing the sample and a peristaltic pump 260 for conveying the sample and/or a fluid within the cartridge 100 and/or the analyzer 200, characterized in that the pump 260 is constructed according to any of the preceding aspects.

What is claimed is:

1. A peristaltic pump for conveying a fluid within a cartridge, comprising:

a motor; and a pump head configured to be rotated about a central axis by means of the motor, wherein the pump head comprises a main body, a plurality of rollers for contacting the cartridge and a plurality of brackets for the rollers, wherein each of the rollers is mounted to one of the brackets and is configured to be rotated about a roller axis, wherein each of the brackets is mounted to the main body and is configured to be pivoted about a pivot axis relative to the main body, and wherein each pivot axis runs through an associated roller.

2. The pump according to claim 1, wherein each of the rollers comprises a cone shaped roller including a free end that is turned towards the central axis.

3. The pump according to claim 1, wherein each roller comprises a cone-shaped roller head and a roller shaft.

4. The pump according to claim 1, wherein each of the brackets comprises a pair of pivots, wherein each pair of pivots define one pivot axis.

5. The pump according to claim 4, wherein the main body comprises a plurality of sockets and includes at least one of the following features: each of the sockets is configured to pivotably receive at least one of the pivots; or each of the pivots is clipped in one of the sockets.

6. The pump according to claim 5, wherein each of the pivots comprises a stop limiting pivoting movement of the rollers.

7. The pump according to claim 1, wherein the rollers being clipped in the brackets and the brackets being clipped in the main body.

8. The pump according to claim 1, wherein the pump comprises a plurality of roller bearings.

9. The pump according to claim 8, wherein each of the roller bearings is clipped in one of the brackets.

10. The pump according to claim 8, wherein each of the brackets comprises a receptacle for receiving one of the roller bearings.

11. The pump according to claim 8, wherein each of the rollers comprises a bearing surface for the roller bearings, each roller being clipped into one of the roller bearings with its bearing surface.

12. The pump according to claim 1, the pump further comprising a coupling apparatus for connecting the pump head to the motor, wherein the coupling apparatus is constructed as a beam coupling, wherein the coupling apparatus comprises an outer spring for a tumbling motion of the pump head and an inner spring for an axial motion of the pump head.

13. The pump according to claim 12, wherein the coupling apparatus is flexible and configured to compensate for misalignment and an offset between the pump head and the motor.

14. The pump according to claim 12, wherein the outer spring is formed by the wall of the coupling apparatus.

* * * * *